US006821951B2

(12) United States Patent
Schwier et al.

(10) Patent No.: US 6,821,951 B2
(45) Date of Patent: Nov. 23, 2004

(54) PROCESSES FOR MAKING PHARMACEUTICAL ORAL ECB FORMULATIONS AND COMPOSITIONS

(75) Inventors: John Richard Schwier, Brownsburg, IN (US); Jerry Taylor, Indianapolis, IN (US)

(73) Assignee: Eli Lilly and Company, Indianapolis, IN (US)

(*) Notice: Subject to any disclaimer, the term of this patent is extended or adjusted under 35 U.S.C. 154(b) by 85 days.

(21) Appl. No.: 09/942,435

(22) Filed: Aug. 29, 2001

(65) Prior Publication Data

US 2002/0151474 A1 Oct. 17, 2002

Related U.S. Application Data

(63) Continuation of application No. PCT/US00/05547, filed on Mar. 2, 2000.
(60) Provisional application No. 60/122,693, filed on Mar. 3, 1999.

(51) Int. Cl.[7] ............................................... A61K 38/00
(52) U.S. Cl. ............... 514/9; 514/8; 514/7; 514/217.05
(58) Field of Search ....................... 514/9, 8, 7, 217.05

(56) References Cited

U.S. PATENT DOCUMENTS

| | | | |
|---|---|---|---|
| 3,293,482 A | 12/1966 | Wolkstein | |
| 3,978,210 A | 8/1976 | Mizuno et al. | |
| 4,293,482 A | 10/1981 | Abbott et al. | |
| 4,293,483 A | 10/1981 | Debono | |
| 4,293,489 A | 10/1981 | Debono | |
| 4,299,763 A | 11/1981 | Abbott et al. | |
| 4,304,716 A | 12/1981 | Abbott et al. | |
| 4,320,052 A | 3/1982 | Abbott et al. | |
| 4,876,241 A | 10/1989 | Feldman et al. | |
| 5,166,135 A | 11/1992 | Schmatz | |
| 5,198,421 A | 3/1993 | Chen et al. | |
| 5,202,309 A | 4/1993 | Schwartz et al. | |
| 5,541,160 A | 7/1996 | Balkovec et al. | |
| 5,573,936 A | 11/1996 | Kreuzman et al. | |
| 5,618,787 A | 4/1997 | Jamison et al. | |
| 5,629,289 A | 5/1997 | Rodriguez | |
| 5,629,290 A | 5/1997 | LaGrandeur et al. | |
| 5,646,111 A | 7/1997 | Borromeo et al. | |
| 5,652,213 A | 7/1997 | Jamison et al. | |
| 5,693,611 A | 12/1997 | Henle et al. | |
| 5,696,084 A * | 12/1997 | Lartey et al. .................. | 514/9 |
| 5,786,325 A | 7/1998 | Borromeo et al. | |
| 5,932,543 A | 8/1999 | Burkhardt et al. | |
| 5,965,525 A | 10/1999 | Burkhardt et al. | |
| 5,972,996 A * | 10/1999 | Nielsen-Kahn et al. ...... | 514/456 |
| 6,043,341 A | 3/2000 | Udodong et al. | |
| 6,258,821 B1 | 7/2001 | Stogniew et al. | |
| 6,323,176 B1 | 11/2001 | Jamison et al. | |
| 6,384,013 B1 | 5/2002 | Burkhardt et al. | |
| 6,506,726 B1 | 1/2003 | Dobbins et al. | |
| 2002/0160942 A1 * | 10/2002 | Larew et al. ................ | 514/8 |
| 2002/0161176 A1 | 10/2002 | Dalder et al. | |
| 2003/0054981 A1 * | 3/2003 | Milton et al. ................. | 514/7 |

FOREIGN PATENT DOCUMENTS

| | | |
|---|---|---|
| CA | 2043762 | 12/1991 |
| EP | 0 031 221 A1 | 7/1981 |
| EP | 0 359 529 A1 B1 | 3/1990 |
| EP | 0 447 186 A1 | 9/1991 |
| EP | 0 448 353 A2 A3 | 9/1991 |
| EP | 0 462 531 A2 B1 | 12/1991 |
| EP | 0 460 882 A2 A3 B1 | 12/1991 |
| EP | 0 561 639 A1 B1 | 9/1993 |
| EP | 0 589 074 | 3/1994 |
| EP | 0 744 405 | 11/1996 |
| EP | 0 757 058 | 2/1997 |
| EP | 0 931 834 | 7/1999 |
| JP | 03 240727 | 10/1991 |
| JP | 05 271097 | 10/1993 |
| JP | 06 172205 | 6/1994 |
| WO | WO 94/25084 | 11/1994 |
| WO | WO 96/31228 A1 | 10/1996 |
| WO | WO 96/37509 A1 | 11/1996 |
| WO | WO 96/37510 A1 | 11/1996 |
| WO | WO 96/37511 A1 | 11/1996 |
| WO | WO 96/37512 A1 | 11/1996 |
| WO | WO 97/05163 A1 | 2/1997 |
| WO | WO 97/27864 A1 | 8/1997 |
| WO | WO 97/30695 | 8/1997 |
| WO | WO 99/06062 A1 | 2/1999 |
| WO | WO 99/43337 A1 | 9/1999 |
| WO | WO 00/12540 A1 | 3/2000 |
| WO | WO 00/11023 A2 A3 | 3/2000 |
| WO | WO 00/35944 A1 | 6/2000 |
| WO | WO 00/35945 A1 | 6/2000 |
| WO | WO 00/34315 A2 A3 | 6/2000 |
| WO | WO 00/51564 A1 | 9/2000 |
| WO | WO 00/51567 A1 | 9/2000 |
| WO | WO 00/52036 A1 | 9/2000 |
| WO | WO 00/52037 A1 | 9/2000 |

OTHER PUBLICATIONS

Etter, M.C. and Baures, P.W. (1988) "Triphenylphosphine Oxide as a Crystallization Aid," *J. Am. Chem. Soc.* 110:639–640.

Ibrahim, F. S. et al., (1995) "The Effect of pH, sugars and calcium ion concentration on the thermal stability of whey proteins" *Egyptian J. Dairy Sci.* 23:177–178.

Nail, S.L. and Gatlin, L. A. (1993) "Chapter 3: Freeze drying: Principles and practice" *Pharmaceutical Dosage Forms*, Parenteral Medications, vol. 2, 2nd Edition, edited by Kenneth, E. A. et al., Marcel Dekker, Inc., pp. 163–233.

(List continued on next page.)

*Primary Examiner*—Christopher R. Tate
*Assistant Examiner*—Maury Audet
(74) *Attorney, Agent, or Firm*—Morrison & Foerster LLP

(57) ABSTRACT

A fluid bed spray process is described where one or more carbohydrates are incorporated into an echinocandin formulation to provide a significant improvement in thermal stability. The carbohydrate is solubilized with an echinocandin compound or echinocandin/carbohydrate complex in a solvent(s) to form a pharmaceutical solution which is sprayed onto the surface of a granular diluent or carrier. The resulting granular oral formulations and medicaments derived therefrom are also described.

21 Claims, No Drawings

OTHER PUBLICATIONS

Avis, K. E. (1990). "Parenteral Preparations" Chapter 84 *In Remington Pharmaceutical Sciences*, 18th edition, Mack Publishing Company p. 1545–1569.

Longer, M. A. and Robinson, J. R. (1990). "Transdermal Systems" in Chapter 91 *In Remington Pharmaceutical Sciences*, 18th edition, Mack Publishing Company. p. 1690–1693.

Nema, S. et al. (1997). "Excipients and Their Use in Injectable Products," *PDA Journal of Pharm. Science and Tech.* 51(4):166–171.

Sclarra, J. J. and Cutie, A. J. (1990). "Aerosols" Chapter 92 *In Remington Pharmaceutical Sciences*. 18th edition, Mack Publishing Company. p. 1694–1712.

Turco, S. J. (1990). "Intravenous Admixtures," Chapter 85 *In Remington Pharmaceutical Sciences*, 18th edition, Mack Publishing Company. p. 1570–1580.

\* cited by examiner

PROCESSES FOR MAKING PHARMACEUTICAL ORAL ECB FORMULATIONS AND COMPOSITIONS

CROSS-REFERENCE TO RELATED APPLICATIONS

This application is a continuation of International Patent Application No. PCT/US00/05547, filed on Mar. 2, 2000, which claims the benefit of U.S. Provisional Patent Application Ser. No. 60/122,693, filed on Mar. 3, 1999, the contents of which are incorporated herein by reference in their entirety.

FIELD OF THE INVENTION

The present invention relates to processes for making pharmaceutical formulations or compositions containing an antifungal compound, in particular, the incorporation of an echinocandin/carbohydrate complex into an oral formulation or composition to enhance stability.

BACKGROUND OF THE INVENTION

Oral formulations of pharmaceutical drugs may be administered to patients via sachets, chewable or conventional tablets, capsules or oral solutions and suspensions. The formulation that is developed for a particular drug is dependent on a variety of issues. For example, it is well-known in the art that an oral formulation should be sufficiently stable, have an acceptable appearance and be prepared from generally accepted, safe excipients.

Stability is an important consideration when designing a formulation, especially for oral applications. For practical and commercial reasons, it is desirable to maintain sufficient formulation stability for at least two years. Therefore, a primary formulation design goal is to optimize shelf-life and stability at the selected storage condition (e.g., room temperature).

The instability of the echinocandin compounds make them particularly difficult to formulate. Most of the formulations tested to date have a shelf life of less than one year at room temperature. Generally, a shelf life of at least two years is desirable. Therefore, there is a need for an oral formulation containing an echinocandin compound having improved thermal stability.

SUMMARY OF THE INVENTION

Applicants have discovered that the incorporation of one or more carbohydrates into an echinocandin formulation at specific process stages provides a significant improvement in thermal stability. In one embodiment of the present invention, a process is provided for preparing an oral pharmaceutical formulation which comprises (i) mixing an echinocandin compound or a echinocandin/carbohydrate complex and at least one carbohydrate in a solvent or mixture of solvents to form a pharmaceutical solution; (ii) spraying the solution onto a layer of fluidized granular diluent or carrier (e.g., a granular carbohydrate); and (iii) removing the excess solvent or solvents. The pharmaceutical solution may optionally contain surfactants, flavorings, colorants and/or processing aids. Oral granular pharmaceutical formulations prepared by the process described above are also provided, as well as medicaments prepared therefrom such as sachets and chewable tablets.

In another embodiment of the present invention, a process is provided for preparing an oral pharmaceutical formulation comprising the steps of: (i) mixing an echinocandin compound or echinocandin/carbohydrate complex, at least one carbohydrate, and a soluble granulating agent (e.g., polyvinylpyrrolidone) in a solvent or mixture of solvents to form a pharmaceutical solution; (ii) spraying the solution onto a layer of fluidized non-granular diluent or carrier (e.g., carbohydrate powders); and (iii) removing the excess solvent or solvents. The pharmaceutical solution may optionally contain surfactants, flavorings, colorants and/or processing aids. Oral granular pharmaceutical formulations prepared by the process described above are also provided, as well as medicaments prepared therefrom such as sachets and chewable tablets.

In yet another embodiment of the present invention, a method is provided for treating a fungal infection in a mammal in need thereof which comprises administering an oral formulation prepared by one of the processes described above to the mammal.

The term "echinocandin" refers to a compound having the following general structure:

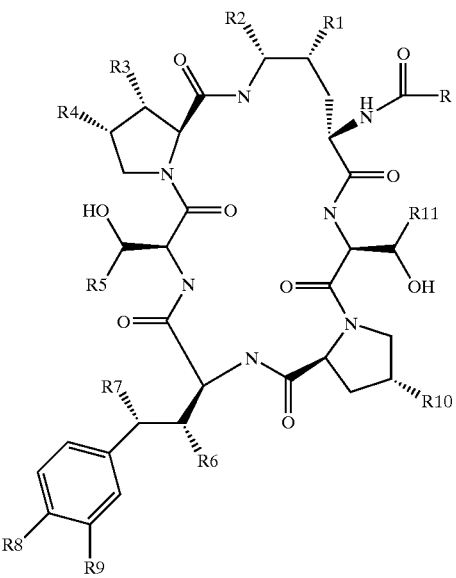

wherein:

R is an alkyl group, an alkenyl group, an alkynyl group, an aryl group, heteroaryl group, or combinations thereof;

$R_1$, $R_2$, $R_3$, $R_6$, $R_7$, and $R_{10}$ are independently hydroxy or hydrogen;

$R_4$ is hydrogen, methyl or —$CH_2C(O)NH_2$;

$R_5$ and $R_{11}$ are independently methyl or hydrogen;

$R_8$ is —OH, —$OPO_3H_2$, —$OPO_3HCH_3$, —$OPO_2HCH_3$, or —$OSO_3H$; and $R_9$ is —H, —OH, or —$OSO_3H$.

"Echinocandin B" or "ECB" refers to a echinocandin compound as described above where $R_1$, $R_2$, $R_3$, $R_6$, $R_7$, $R_8$, and $R_{10}$ are hydroxy groups; $R_4$, $R_5$, and $R_{11}$ are methyl groups; $R_9$ is a hydrogen. In the natural product, R is a linoleoyl group. In a particularly useful semi-synthetic compound, R has both a rigid and a flexible component, for example, a compound where R is represented by the following formula

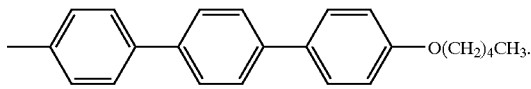

The term "alkyl" refers to a hydrocarbon radical of the general formula $C_nH_{2n+1}$ containing from 1 to 30 carbon atoms unless otherwise indicated. The alkane radical may be straight, branched, cyclic, or multi-cyclic. The alkane radical may be substituted or unsubstituted. Similarly, the alkyl portion of an alkoxy group or alkanoate have the same definition as above.

The term "alkenyl" refers to an acyclic hydrocarbon containing at least one carbon-carbon double bond. The alkene radical may be straight, branched, cyclic, or multi-cyclic. The alkene radical may be substituted or unsubstituted.

The term "alkynyl" refers to an acyclic hydrocarbon containing at least one carbon carbon triple bond. The alkyne radical may be straight, or branched. The alkyne radical may be substituted or unsubstituted.

The term "aryl" refers to aromatic moieties having single (e.g., phenyl) or fused ring systems (e.g., naphthalene, anthracene, phenanthrene, etc.). The aryl groups may be substituted or unsubstituted. Substituted aryl groups include a chain of aromatic moieties (e.g., biphenyl, terphenyl, phenylnaphthalyl, etc.)

The term "heteroaryl" refers to aromatic moieties containing at least one heteroatom within the aromatic ring system (e.g., pyrrole, pyridine, indole, thiophene, furan, benzofuran, imidazole, pyrimidine, purine, benzimidazole, quinoline, etc.). The aromatic moiety may consist of a single or fused ring system. The heteroaryl groups may be substituted or unsubstituted.

"Echinocandin/carbohydrate complex" refers to a crystalline complex formed between an echinocandin compound and a carbohydrate when the echinocandin is crystallized or recrystallized from a solvent in the presence of the carbohydrate. A more detailed description of the echinocandin/carbohydrate complexes may be found in Larew, et al., filed on Mar. 3, 1999 entitled "Echinocandin/Carbohydrate Complexes" and incorporated herein by reference.

"Carbohydrate" refers to an aldehydic or ketonic derivative of polyhydric alcohols represented by the formulas $C_n(H_2O)_n$ (e.g., glucose, $C_6(H_2O)_6$; sucrose, $C_{12}(H_2O)_{11}$). Carbohydrates include compounds with relatively small molecules, such as the simple sugars (e.g., monosaccharides, disaccharides, etc.), as well as macromolecular (polymeric) substances such as starch, glycogen, and cellulose polysaccharides. Sugars are carbohydrates (saccharides) having the general composition $(CH_2O)_n$ and simple derivatives thereof. Although the simple monomeric sugars (glycoses) are described as polyhydroxy aldehydes or ketones, e.g., $HOCH_2-(CHOH)_4-CHO$ for aldohexoses (e.g., glucose) or $HOCH_2-(CHOH)_3-COCH_2OH$ for 2-ketoses (e.g., fructose), the structures are commonly written as five (furanose) or six(pyranose) membered ring cyclic ethers, e.g.

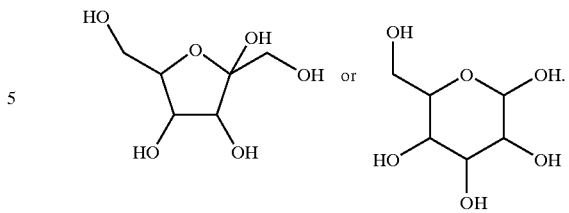

The term "granular" diluents or carriers refer to materials where approximately 70% by weight of the material has a particle size greater than 150 microns.

The term "non-granular" or "powder" diluents or carriers refer to materials where approximately 70% by weight of the material has a particle size less than 150 microns.

The term "granulating agent" refers to a binder that causes the diluent or carrier to bind together to form larger aggregates or granules upon spraying the agent onto the diluent powder surface in the presence of a solvent or solvents.

DETAILED DESCRIPTION

Applicants have discovered that the stability of an oral echinocandin formulation or composition may be enhanced by incorporating the echinocandin compound into the pharmaceutical composition as an echinocandin/carbohydrate complex or by forming an echinocandin/carbohydrate complex in situ. For example, the echinocandin/carbohydrate complex may be formed in situ by mixing the echinocandin compound with the carbohydrate in a suitable solvent to provide a pharmaceutical solution which is then sprayed onto a fluidized bed of granules. Alternatively, the echinocandin/carbohydrate pharmaceutical solution may be sprayed onto a fluidized bed of non-granular (or powder) diluent or carrier. Preferably, a granulating agent is added to the spray solution to bind the powder together to form larger aggregates or granules in the presence of the solvent or solvents. To perform most effectively, the granulating agent should be soluble in the solvent system used in the pharmaceutical solution. For an acetone/water solvent system, a preferred granulating agent is polyvinylpyrrolidone (e.g., Povidone™ available from BASF Corp.).

Suitable carbohydrates include adonitol, arabinose, arabitol, ascorbic acid, chitin, D-cellubiose, 2-deoxy-D-ribose, dulcitol, (S)-(+)-erythrulose, fructose, fucose, galactose, glucose, inositol, lactose, lactulose, lyxose, maltitol, maltose, maltotriose, mannitol, mannose, melezitose, melibiose, microcrystalline cellulose, palatinose, pentaerythritol, raffinose, rhamnose, ribose, sorbitol, sorbose, starch, sucrose, trehalose, xylitol, xylose and hydrates thereof. Suitable carbohydrates also include the D and L enantiomers, as well as the alpha and beta anomers of the compounds listed above. Preferred carbohydrates are the simple sugars (e.g., mono- and di-saccharides). Particularly useful sugars include L-arabinose, D-arabitol, L-arabitol, 2-deoxy-D-ribose, (S)-(+)-erythrulose, D-fructose, D-(+)-fucose, L-fucose, D-galactose, β-D-glucose, D-lyxose, L-lyxose, D-maltose, maltotriose, melezitose, palatinose, D-raffinose, D-sorbitol, D-trehalose, xylitol, L-xylose and hydrates thereof When an echinocandin/carbohydrate complex is used, the added carbohydrate may or may not be the same as the carbohydrate in the complex.

Suitable solvents include any solvent, or mixture of solvents, inert to the ongoing process that sufficiently solubilizes the echinocandin and carbohydrate materials to afford a medium which can be used in the fluid bed spray process (typically, protic or ketone solvents). A preferred solvent system used for the pharmaceutical spray solution is a mixture of water and acetone. While any percent mixture of water and acetone can be used that will solubilize the echinocandin or echinocandin/carbohydrate complex and carbohydrate, the preferred percentage of acetone is from about 50% to 70% on a volume basis.

Suitable granular and non-granular (or powder) materials include the carbohydrates described above as well as cellulose/starch materials, polyethylene glycol 4000, 6000 and 8000 (e.g., the higher melting solid PEG series; available from Union Carbide Corp.), hydroxypropyl methylcellulose (HPMC; available from Shin-Etsu Chemical Co. Ltd.), hydroxypropyl methylcellulose phthalates (e.g., HP-50, HP-55, HP-55S; also available from Shin-Etsu Chemical Co. Ltd), and dextrates (e.g., Emdex™; available from Edward Mendell Co. Inc. and Dextrin™; available from Matheson Colleman & Bell). Preferred granular or non-granular materials are the carbohydrates such as fructose, glucose, lactose, lactulose, maltitol, maltose, maltotriose, mannitol, mannose, microcrystalline cellulose, HPMC, HPMC Phthalate, dextrates, dextrin, sorbitol, sorbose, starch and starch derivatives, sucrose, trehalose, xylitol, xylose and hydrates thereof. Suitable carbohydrates also include the D and L enantiomers, as well as the alpha and beta anomers. Most preferred are the low moisture mono- and di-saccharides, such as mannitol (e.g., Mannogen™ 2080, available from SPI Polyols, Inc., New Castle, Del.), lactose and maltose.

The pharmaceutical solution is sprayed onto the fluidized granular or non-granular carrier in a fluid bed granulator/dryer (e.g., Glatt GPCG-3, available from Glatt Air Techniques, Inc., Ramsey, N.J.). Although not wishing to be bound by any particular theory, it is believed that the sprayed pharmaceutical solution forms an in situ echinocandin/carbohydrate complex on the surface of the fluidized carrier upon drying. The echinocandin compound is generally present in the final sprayed granules at a weight percentage from about 5% to 25%, preferably from 7% to 20%, more preferably from 12% to 16%. The carbohydrate used in the pharmaceutical solution is generally present in the final sprayed granules at a weight percentage from about 5% to 25%, preferably from about 7% to 20%, more preferably from about 12% to 16%. The granular or non-granular carrier is generally present in the final sprayed granules at a weight percentage from about 50% to 90%, preferably from about 60% to 80%, more preferably from about 65% to 75%.

Applicants have observed that the final sprayed granules exhibit better thermal stability and enhanced flowability compared to the starting bulk echinocandin material alone. (see, Example 1) Even though one of the major excipients of the formulation (i.e., fluidized carbohydrate—a potential echinocandin stabilizer) is not part of the solution containing the pharmaceutically active compound, the sprayed granules still exhibit enhanced stability.

The relative thermal storage stability of the fluid bed spray granules was assessed and compared to that of the starting echinocandin bulk. HPLC analysis of the starting echinocandin bulk and of the final spray granules was run to determine the initial level of degradation products, often referred to as % total related substances (i.e. % TRS). Both samples were then stored in separate high density polyethylene (HDPE) bottles with wax vinyl aluminum foil (WVAF) cap seals for 1 and 2 weeks at 40° C. The increase in % TRS was measured by HPLC at the two time points.

Table 1 shows the change in % TRS between bulk ECB compound and a trial process for ECB granules prepared by the fluid bed spray process described above.

TABLE 1

| Storage Conditions* | Starting ECB bulk Compound (% TRS) | FB Spray Granules (% TRS) |
|---|---|---|
| Initial | 4.94% | 5.12% |
| 1 Week at 40° C. | +2.86% | +1.38% |
| 2 Weeks at 40° C. | +3.85% | +2.30% |

*Each of the samples were stored in brown opaque HDPE bottles closed with WVAF caps.

The FB spray process did not significantly increase the %TRS of the sprayed granules. It is important to note that the FB spray granules containing the in-situ formed echinocandin/carbohydrate complex showed enhanced storage stability (i.e. lower % TRS increases) at 1 and 2 weeks of storage at 40° C. relative to the starting echinocandin bulk compound.

Table 2 shows the change in %TRS between bulk ECB compound and a second trial process for ECB granules prepared by the fluid bed spray process described above.

TABLE 2

| Storage Conditions* | Starting ECB bulk Compound (% TRS) | FB Spray Granules (% TRS) |
|---|---|---|
| Initial | 5.36% | 5.64% |
| 1 Week at 40° C. | +3.46% | +1.10% |
| 2 Weeks at 40° C. | +4.29% | +2.51% |

*Each of the samples were stored in brown opaque HDPE bottles closed with WVAF caps.

Again, the FB spray process did not significantly increase the % TRS of the sprayed granules. The FB spray granules containing the in-situ formed echinocandin/carbohydrate complex showed enhanced storage stability (i.e. lower % TRS increases) at 1 and 2 weeks of storage at 40° C. relative to the starting echinocandin bulk compound. In addition to the enhanced stability of the FB spray granules, improved mixability and flowability of the final FB spray granules was observed.

The sprayed granules may be used to prepare a pharmaceutical medicament that can be orally administered to a patient in need of therapeutic treatment for which the product is designed. For example, the sprayed granules may be contained in a sachet or capsule, or compressed into a tablet. The final spray granules can be readily filled directly into sachet packages, or alternatively, can be readily mixed with additional excipients prior to forming into tablets, filling into capsules or filling into bottles.

For example, the sprayed granules can be dry mixed with flavoring agent(s), tablet disintegrant (e.g. Croscarmellose sodium; available from FMC Corp.), processing aid(s) (e.g. Syloid 63FP; silicon dioxide available from Grace-Davison, Baltimore Md.) and tablet lubricants such as stearic acid (available from Witco Corp.) or glyceryl behenate (available from Gattefosse Corp.) prior to being compressed into tablets (chewable) using standard tabletting equipment and technology. (see i.e., "Oral Solid Dosage Forms", Remington's Pharmaceutical Sciences, Chapter 90, Mack Publishing Co., Pennsylvania, 1985.)

Chewable tablets may be produced using standard procedures well known to those skilled in the art. Generally, chewable tablets contain flavoring agents (e.g. peppermint oil, menthol, or wintergreen oil, etc.) at levels between about 0.1% to 2.0% based on total final tablet weight (preferably between about 0.2% and 0.6% by weight) which may be added to the echinocandin/carbohydrate pharmaceutical solution prior to spraying the granules. Sweeteners are also generally added to chewable tablets. However, in the present invention, the carbohydrates used in the formulation may provide sufficient sweetening such that additional sweeteners may not be necessary. The use of mannitol or maltose as the carrier in the formulation would also supply additional sweetening plus the proper "mouth-feel"/"coolness" and texture for chewable tablets. Other ingredients may also be added by dry mixing (e.g. tumble bin or ribbon mixer) with the sprayed granules to give the final granulation mix. The final granulation mix is then compressed into tablets. Unlike conventional tablets, larger tooling (e.g. Pillow shaped No. 800 tooling) is generally used in the production of chewable tablets.

In addition to the materials already discussed, the oral formulations or medicaments of the present invention may also include other carriers, diluents and excipients which are well known to those skilled in the art and include materials such as waxes, water soluble and/or swellable polymers, hydrophilic or hydrophobic materials, gelatin, oils, solvents, water, and the like. The particular carrier, diluent or excipient used will depend upon the means and purpose for which the active ingredient is being applied. The formulations may also include wetting agents, lubricating agents, emulsifiers, suspending agents, preservatives, perfuming agents, colorants, opaquing agents, glidants, processing aids and combinations thereof.

The cyclic peptides used in the present invention may be produced by culturing various microorganisms. Suitable natural product starting materials belonging to the echinocandin cyclic peptide family include Echinocandin B, Echinocandin C, Echinocandin D, Aculeacin $A_7$, Mulundocandin, Sporiofungin A, Pneumocandin $A_0$, WF11899A, and Pneumocandin $B_0$. In general, the cyclic peptides may be characterized as a cyclic hexapeptide nucleus with an acylated amino group on one of the amino acids. The amino group on the naturally-occuring cyclic peptide is typically acylated with a fatty acid group forming a side chain off the nucleus. Examples of naturally-occurring acyl groups include linoleoyl (Echinocandin B, C and D), palmitoyl (Aculeacin Aγ and WF11899A), stearoyl, 12-methylmyristoyl (Mulundocandin), 10,12-dimethylmyristoyl (Sporiofungin A and Pneumocandin $A_0$) and the like.

Semi-synthetic derivatives may be prepared by removing the fatty acid side chain from the cyclic peptide nucleus to produce a free amino group (i.e., no pendant acyl group —C(O)R). The free amine is then reacylated with a suitable acyl group. For example, the echinocandin B nucleus has been re-acylated with certain non-naturally occurring side chain moieties to provide a number of antifungal agents. See, i.e., U.S. Pat. No. 4,293,489 (Debono). Those skilled in the art will appreciate that the N-acyl side chain encompasses a variety of side chain moieties known in the art. Suitable side chain moieties include substituted and unsubstituted alkyl groups, alkenyl groups, alkynyl groups, aryl groups, heteroaryl groups and combinations thereof. Preferably, the side chain contains both a linearly rigid section and a flexible alkyl section to maximize antifingal potency. Representative examples of preferred acyl side chains include R groups having the following structures:

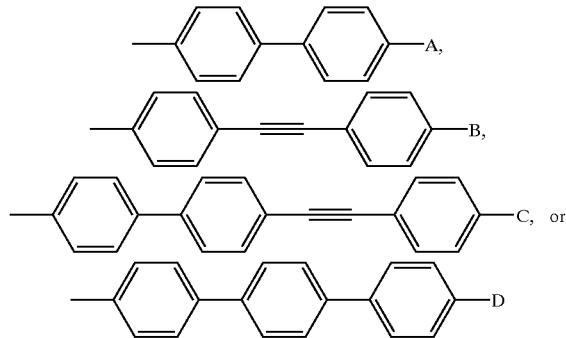

where A, B, C and D are independently hydrogen, $C_1$-$C_{12}$ alkyl, $C_2$-$C_{12}$ alkynyl, $C_1$-$C_{12}$ alkoxy, $C_1$-$C_{12}$ alkylthio, halo, or —O—$(CH_2)_m$—[O—$(CH_2)_n]_p$—O—($C_1$-$C_{12}$ alkyl) or —O—$(CH_2)_q$—X-E;

m is 2, 3 or 4; n is 2, 3 or 4; p is 0 or 1; q is 2, 3 or 4;

X is pyrrolidino, piperidino or piperazino; and E is hydrogen, $C_1$-$C_{12}$ alkyl, $C_3$-$C_{12}$ cycloalkyl, benzyl or $C_3$-$C_{12}$ cycloalkylmethyl.

As noted above, the cyclic peptides described herein may be prepared by fermentation of known microorganisms as described in the art. The subsequent deacylation is typically carried out enzymatically using a deacylase enzyme by known materials and procedures described in the art.

For example, U.S. Pat. No. 3,293,482 (Abbott et al.), incorporated herein by reference, describes the deacylation and preparation of the cyclic peptide of formula I where $R_4$, $R_5$, and $R_{11}$ are methyl, $R_9$ is hydrogen, and $R_1$, $R_2$, $R_3$, $R_6$, $R_7$, $R_8$ and $R_{10}$ are each hydroxy. U.S. Pat. No. 4,299,763 (Abbott et al.), incorporated herein by reference, describes the deacylation and preparation of the cyclic peptide of formula I where $R_4$, $R_5$, and $R_{11}$ are methyl, $R_2$ is hydroxy, $R_7$ and $R_9$ are hydrogen and $R_1$, $R_3$, $R_6$, $R_8$ and $R_{10}$ are each hydroxy. U.S. Pat. No. 3,978,210 (Mizuno et al.), incorporated herein by reference, describes the preparation of aculeacin. U.S. Pat. No. 4,304,716, incorporated herein by reference, describes the deacylation and preparation of the cyclic peptide of formula I where $R_5$ is —$CH_2C(O)NH_2$; $R_{11}$ is methyl; $R_4$ and $R_9$ are hydrogen; $R_1$, $R_2$, $R_3$, $R_6$, $R_7$, $R_8$ and $R_{10}$ are each hydroxy and the acyl group with substituent R is myristoyl.

Cyclic peptides where $R_2$ and $R_7$ are each hydrogen may be prepared by subjecting the corresponding compound (where $R_2$ and $R_7$ are each hydroxy; the ornithine alpha-amino group may be a free amino group or acylated) to a strong acid and a reducing agent at a temperature of between –5° C. and 70° C., in a suitable solvent. Suitable strong acids include trichloroacetic acid, trifluoroacetic acid or boron trifluoride etherate. A preferred strong acid is trifluoroacetic acid. Suitable reducing agents include sodium cyanoborohydride or triethylsilane. A preferred reducing agent is triethylsilane. Suitable solvents include methylene chloride, chloroform or acetic acid, preferably methylene chloride. The strong acid is present in an amount from about 2 to 60 mol per mol of substrate, and the reducing agent is present in an amount from about 2 to 60 mol per mol of substrate. The acid reduction process selectively removes the aminal ($R_2$) and benzylic ($R_7$) hydroxy groups.

Acylation of the α-amino group on the ornithine unit may be accomplished in a variety of ways well known to those skilled in the art. For example, the amino group may be acylated by reaction with an appropriately substituted acyl halide, preferably in the presence of an acid scavenger such as a tertiary amine (e.g., triethylamine). The reaction is typically carried out at a temperature between about −20° C. to 25° C. Suitable reaction solvents include polar aprotic solvents, such as dioxane or dimethylfornamide. Solvent choice is not critical so long as the solvent employed is inert to the ongoing reaction and the reactants are sufficiently solubilized to effect the desired reaction.

The amino group may also be acylated by reaction with an appropriately substituted carboxylic acid, in the presence of a coupling agent. Suitable coupling agents include dicyclohexylcarbodiimide (DCC), N,N'-carbonyldiimidazole, bis(2-oxo-3-oxazolidinyl)phosphinic chloride (BOP-Cl), N-ethoxycarbonyl-2-ethoxy-1,2-dihydroquinoline (EEDQ), benzotriazole-1-yloxy-tripyrrolidinophosphonium hexafluorophosphate (PyBOP) and the like.

Alternately, the amino group may be acylated with an activated ester of a carboxylic acid such as p-nitrophenyl, 2,4,5-trichlorophenyl, hydroxybenzotriazole hydrate ($HOBT \cdot H_2O$), pentafluorophenol, and N-hydroxysuccinimide carboxylate esters. Preferred acylating moieties are the 2,4,5-trichlorophenyl and HOBT carboxylate esters. The reaction is typically ran 1 to 65 hours at a temperature from about 0° C. to 30° C. in an aprotic solvent. The reaction is generally complete after about 24 to 48 hours when carried out at a temperature between about 15° C. to 30° C. Suitable solvents include tetrahydrofuran and dimethylformamide or mixtures thereof. The amino group is generally present in equimolar proportions relative to the activated ester or with a slight excess of the amino group.

The R—COOH precursor acids are prepared by hydrolyzing a nitrile of the formula R—CN or an ester of the formula R—COO($C_1$-$C_4$ alkyl). The nitrile and ester intermediates may be prepared using procedures known in the art. For example, the nitrile and ester intermediates where R is an alkoxy aryl moiety may be prepared using Procedure A or Procedure B, described below.

Procedure A

One equivalent of an alkyl bromide, iodide, or p-toluenesulfonate is added to a mixture containing one equivalent of a base, such as potassium t-butoxide or potassium carbonate ($K_2CO_3$), and one equivalent of an hydroxy aryl compound in 200-300 ml of acetonitrile ($CH_3CN$). The reaction mixture is refluxed for 6 h and then concentrated in vacuo to provide a residue which is dissolved in a $Et_2O$/2$\underline{N}$ NaOH mixture. The resulting layers are separated and the organic layer is dried over magnesium sulfate ($MgSO_4$), filtered and dried to provide the alkoxy aryl product.

Procedure B

Diethylazodicarboxylate (1 equiv.) is added dropwise to a mixture containing an hydroxy aryl compound (1 equiv.), an alkyl alcohol (1 equiv.) and triphenylphosphine (1 equiv.) in 200-300 ml of THF. After 17 h, the solvent is removed in vacuo to provide a residue which is dissolved in $Et_2O$. The resulting mixture is washed with a 2N NaOH solution, dried over $MgSO_4$, filtered and concentrated to provide a product which is then crystallized from a $Et_2O$/pentane mixture or, if the product contains a tertiary amine, the hydrochloride salt is formed and crystallized from a methanol (MeOH)/EtOAc mixture. The nitrile and ester intermediates where R is an alkynyl aryl moiety may be prepared using Procedure C, below.

Procedure C

A mixture containing $Et_2O$ (2 equiv.), palladium dichloride (0.05 equiv.), triphenylphosphine (0.1 equiv.), cuprous iodide (0.025 equiv.) and an alkyne (1 equiv.) is added to one equivalent of an aryl bromide, iodide, or trifluoromethanesulfonate in $CH_3CN$ (600 ml/0.1 mol of aryl reactant), under nitrogen ($N_2$). The resulting mixture is refluxed for 17 h and then the solvent is removed in vacuo to provide a residue which is slurried in 300 ml of $Et_2O$ and then filtered. The filtrate is washed with a 1$\underline{N}$ HCl solution, dried over $MgSO_4$, filtered and then dried to provide the product.

The ester intermediates where R is a terphenyl moiety may be prepared using Procedure D, below.

Procedure D

1. Formation of Boronic Acid Reactant

Butyl lithium (1.2 equivalents) is added to one equivalent of a cold (−78° C.) aryl halide in THF. After 15 minutes, triisopropyl borate (2 equiv.) is added. After 10 minutes, the reaction mixture is warmed to room temperature and quenched by the addition of water ($H_2O$), followed by the addition of 1$\underline{N}$ HCl. The resulting layers are separated and the organic layer is concentrated in vacuo to provide a solid which is collected by filtration and washed with hexane.

2. Formation of Terphenyl Ester

Tetrakis(triphenylphosphine)palladium (0.03 equiv.) is added to a mixture containing an aryl boronic acid (1 equiv.), $K_2CO_3$ (1.5 equiv.) and methyl 4-iodobenzoate (1 equiv.) (or trichlorophenyl ester of iodobenzoate) in $N_2$-purged toluene. The reaction mixture is refluxed for 7 h and then decanted to remove the $K_2CO_3$ and dried in vacuo to provide a residue. This residue is triturated in $CH_3CN$ and filtered to provide the product. The aryl nitriles and esters described above may be converted to the corresponding carboxylic acids by hydrolysis using Procedure E or Procedure F, below.

Procedure E

An aryl nitrile is dissolved in ethanol (EtOH) and an excess of 50% NaOH solution and refluxed for 2 h. Water is added to the reaction mixture until a solid precipitates. This solid is collected by filtration, added to a dioxane/6N HCl mixture and the resulting mixture is refluxed for 17 h. When the reaction is substantially complete, the carboxylic acid product is crystallized by the addition of $H_2O$ and then collected by filtration and dried in vacuo.

Procedure F

An excess of 2$\underline{N}$ NaOH is added to an aryl ester in MeOH, and the resulting solution is refluxed for 5 h and then acidified by the addition of excess HCl. Water is added to the reaction mixture until a solid (carboxylic acid) precipitates. The carboxylic acid is collected by filtration and dried in vacuo.

The carboxylic acids may be converted to the corresponding 2,4,5-trichlorophenyl esters using Procedure G, below. The activated esters are then used to acylate the amino nucleus.

Procedure G

A mixture containing an aryl carboxylic acid (1 equiv.), 2,4,5-trichlorophenol (1 equiv.) and DCC (1 equiv.) in $CH_2Cl_2$ is stirred for 17 h and then filtered. The filtrate is concentrated to provide a residue which is dissolved in $Et_2O$, filtered, and then pentane is added until crystallization begins. The crystals are collected by filtration and dried in vacuo.

Alternatively, the carboxylic acid may be activated by conversion to the corresponding hydroxybenzotriazole ester using Procedure H, below.

Procedure H

An aryl carboxylic acid (1 equiv.) and a slight excess of N-mesylate substituted hydroxybenzotriazole (1.2 equiv.) were reacted in the presence of a slight excess of a base such as triethylamine ($Et_3N$) (1.3 equiv.) in DMF, under $N_2$. When the reaction was complete, the mixture was diluted with toluene and washed with $H_2O$. The organic portion was diluted with $H_2O$ and then filtered using t-butyl methyl ether (MTBE) for transferring the material. The resultant solid was washed with MTBE and then dried in vacuo.

The echinocandin compound may be isolated and used per se or in the form of its pharmaceutically acceptable salt or hydrate. The term "pharmaceutically acceptable salt" refers to non-toxic acid addition salts derived from inorganic and organic acids. Suitable salt derivatives include halides, thiocyanates, sulfates, bisulfates, sulfites, bisulfites, arylsulfonates, alkylsulfates, phosphonates, monohydrogenphosphates, dihydrogenphosphates, metaphosphates, pyrophosphonates, alkanoates, cycloalkylalkanoates, arylalkonates, adipates, alginates, aspartates, benzoates, fumarates, glucoheptanoates, glycerophosphates, lactates, maleates, nicotinates, oxalates, palmitates, pectinates, picrates, pivalates, succinates, tartarates, citrates, camphorates, camphorsulfonates, digluconates, trifluoroacetates, and the like.

Alternatively, the echinocandin compound may be isolated as a Echinocandin/carbohydrate complex. The complexes are formed using standard crystallization procedures such as those typically performed for purifying compounds by recrystallization. The echinocandin material and carbohydrate are dissolved at an elevated temperature (approximately 45 to 60° C., preferably <than 55° C.) in a solvent. The solution is then slowly cooled until the crystallization begins. A seed crystal (such as a previously crystallized complex or an insoluble sugar) may be added to initiate crystallization. Suitable carbohydrates include those listed earlier for the carbohydrates added to the pharmaceutical spray solution. Preferred carbohydrates include L-arabinose, D-arabitol, L-arabitol, 2-deoxy-D-ribose, (S)-(+)-erythrulose, D-fructose, D-(+)-fucose, L-fucose, D-galactose, β-D-glucose, D-lyxose, L-lyxose, D-maltose, maltotriose, melezitose, palatinose, D-raffinose, D-sorbitol, D-trehalose, xylitol, L-xylose and hydrates thereof. Suitable solvents include any solvent, or mixture of solvents, inert to the ongoing reaction that sufficiently solubilizes the reactants to afford a medium within which to effect the desired complexation between the carbohydrate and the echinocandin compound, such as protic or ketone solvents including methanol, ethanol, benzyl alcohol, as well as mixtures of benzyl alcohol with solvents such as methanol, ethanol, n-propanol, isopropanol, n-butanol, 2-butanol, t-butanol, 2-pentanol, 2-methyl-1-propanol, MEK, acetone, ethyl acetate, toluene, acetonitrile, fluorobenzene, methylene chloride, nitromethane, or cyclic ketones such as cyclopentanone and cyclohexanone. Preferred solvents include methanol, ethanol, benzyl alcohol, and mixtures of benzyl alcohol with methyl ethyl ketone, ethyl acetate, and acetonitrile. A more detailed description of echinocandin/carbohydrate complexes and their preparation may be found in Larew, et al., filed on Mar. 3, 1999 entitled "Echinocandin/Carbohydrate Complexes" and incorporated herein by reference.

The active ingredient is typically formulated into pharmaceutical dosage forms to provide an easily controllable dosage of the drug and to give the patient an elegant and easily handleable product. As used herein, the term "unit dose" or "unit dosage" refers to physically discrete units that contain a predetermined quantity of active ingredient calculated to produce a desired therapeutic effect. When a unit dose is administered orally, it is typically provided in the form of a tablet, capsule, pill, powder packet (sachet), wafer, etc. Alternatively, a unit dose may be administered in the form of a liquid solution that can be swished and swallowed, or a dry or liquid aerosol which may be inhaled or sprayed.

The dosage to be administered may vary depending upon the physical characteristics of the patient, the severity of the patient's symptoms, and the means used to administer the drug. The specific dose for a given patient is usually set by the judgment of the attending physician.

Echinocandin and semi-synthetic echinocandin compounds have been shown to exhibit antifungal and antiparasitic activity such as growth inhibition of various infectious fungi including *Candida* spp. (i.e., *C. Albicans, C. Parapsilosis, C. Krusei, C. Glabrata, C. Tropicalis,* or *C. Lusitaniaw*); *Torulopus* spp. (i.e., *T. Glabrata*); *Aspergillus* spp. (i.e., *A. Fumigatus*); *Histoplasma* spp. (i.e., *H. Capsulatum*); *Cryptococcus* spp. (i.e., *C. Neoformans*); *Blastomyces* spp. (i.e., *B. Dermatitidis*); *Fusarium* spp.; *Trichophyton* spp., *Pseudallescheria boydii, Coccidioides immits, Sporothrix schenckii,* etc.

Compounds of this type also inhibit the growth of certain organisms primarily responsible for opportunistic infections in immunosuppressed individuals, such as growth inhibition of *Pneumocystis carinfi* (the causative organism of pneumocystis pneumonia (PCP) in AIDS and other immunocompromised patients. Other protozoans that are inhibited by echinocandin-type compounds include *Plasmodium* spp., *Leishmania* spp., *Trypanosoma* spp., *Cryptosporidium* spp., *Isospora* spp., *Cyclospora* spp., *Trichomnas* spp., *Microsporidiosis* spp., etc.

Consequently, the formulations generated are useful in combating either systemic fungal infections or fungal skin infection. Accordingly, the formulations and processes of the present invention may be used in the manufacture of a medicament for the therapeutic applications described herein. For example, fungal activity (preferably, *Candida albicans* or *Aspergillus fumigatis* activity) or parasitic activity may be inhibited by contacting a pharmaceutical formulation prepared by the present invention with a fungus or parasite, respectively. The term "contacting" includes a union or junction, or apparent touching or mutual tangency of a compound of the invention with a parasite or fungus. The term does not imply any further limitations to the process, such as by mechanism of inhibition. The methods are defined to encompass the inhibition of parasitic and fungal activity by the action of the compounds and their inherent antiparasitic and antifungal properties.

A method for treating a fungal infection which comprises administering an effective amount of a pharmaceutical formulation prepared by the present invention to a host in need of such treatment is also provided. A preferred method includes treating a *Candida albicans* or *Aspergillus fumigatis* infection. The term "effective amount" refers to an amount of active compound which is capable of inhibiting fungal activity. The dose administered will vary depending on such factors as the nature and severity of the infection, the age and general health of the host and the tolerance of the host to the antifungal agent. The particular dose regimen likewise may vary according to these factors. The medicament may be given in a single daily dose or in multiple doses during the day. The regimen may last from about 2-3 days to about 2-3 weeks or longer. A typical daily dose (administered in single or divided doses) contains a dosage level between about 0.01 mg/kg to 100 mg/kg of body weight of an active compound. Preferred daily doses are generally between about 0.1 mg/kg to 60 mg/kg and more preferably between about 2.5 mg/kg to 40 mg/kg.

EXAMPLES

The echinocandin compound used to exemplify the formulations of the present invention was prepared as described in the following preparations. Specifically, the following sequence describes the preparation of anti-fungal compound 1(a) having the following structure:

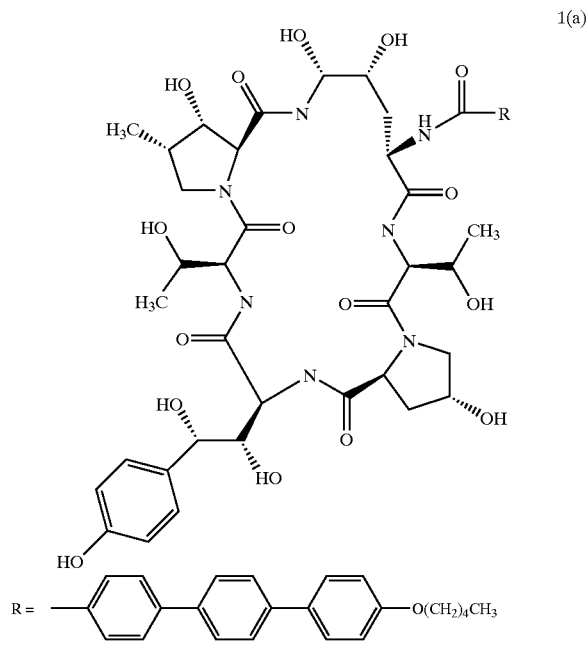

1(a)

It will be understood by those skilled in the art that the following serves as an illustrative example and that other semi-synthetic echinocandin compounds useful as anti-fungal agents may be synthesized using similar procedures or procedures described in references cited earlier in the specification. Materials used in the following preparations are available from Aldrich Chemicals (Milwaukee, Wis.) unless designated otherwise.

Compound Preparations

Preparation of 4-Bromo-4'-pentyloxybiphenyl 1(a):

Anhydrous $K_2CO_3$ (416 g, 3 mol) was added to a mixture of 4-bromo-4'-hydroxybiphenyl (300 g, 1. 2 mol), 1-iodopentane (234 ml, 1.79 mol) and 2-butanone (600 ml). The reaction mixture was refluxed for 44 h until TLC (85:15 hexanes/EtOAc) showed complete consumption of the bromo alcohol. The mixture was cooled to about 30° C., diluted with $CH_2Cl_2$ (600 ml) and then filtered. The filtrate was washed twice with $H_2O$ and twice with a saturated aqueous NaCl solution, dried over anhydrous $Na_2SO_4$, filtered and then dried at reduced pressure to provide a solid. This solid was isolated by filtration, washed repeatedly with a total of 2L of ice-cold heptane to remove all traces of iodopentane and then dried overnight under high vacuum. Yield: 340 g (88%) of a white powder.

Alternative Preparation of 4-bromo-4'-pentyloxybiphenyl 1(a):

4-Bromo-4'-hydroxybiphenyl (12.5 g, 50.2 mmol) was added to a solution of NaOH (2.28 g, 97% pure, 55.2 mmol) in deionized $H_2O$ (150 ml), followed by the addition of 1-iodopentane (11.9 g, 60.2 mmol) and tetrabutylammonium bromide (0.82 g, 2.5 mmol). The mixture was stirred at 90° C. for 3.75 h until the solids went into solution. Then, as the reaction proceeded, the desired product began to precipitate. The mixture was slowly cooled and then filtered to provide a solid which was washed with deionized water until the pH of the filtrate was neutral and then dried for 16 h in a vacuum oven at 30° C. Yield: 15.41 g (96%) of 5a. $R_f$ 0.5 (97:3 hexanes/EtOAc). $^1$H NMR: δ 0.93 (t, 3H, J=6.9 Hz); 1.41 (m, 4H); 1.79 (m, 2H); 3.97 (t, 2H, J=6.6 Hz); 6.98 (m, 2H); 7.23 (m,6H). $^{13}$C NMR: δ 14.03; 22.43; 28.22; 28.98; 68.12; 114.91; 120.71; 127.93; 128.27; 131.77; 132.24; 139.82; 159.03. MS(FAB$^+$): m/z 320. IR(CHCl$_3$): 2960, 2936, 2874, 1608, 1518, 1485, 1475 cm$^{-1}$ Analysis for $C_{17}H_{19}BrO$: Calcd: C, 63.96; H. 6.00; Br, 25.0; Found: C, 64.10; H. 5.97; Br, 25.28.

Preparation of 4-Boronic acid-4 '-pentyloxybiphenyl 2(a):

To a cold (−20° C.) mixture of Compound 1(a) (100 g, 0.31 mol) in t-butylmethylether (MTBE) (1L), was slowly added n-butyl lithium (150 ml of a 2.5M hexanes solution, 0.37 mol) dropwise under $N_2$, while maintaining the internal temperature between −19° and −18° C. The resultant mixture was stirred for 3.5 h between −17° and −16° C. which resulted in a light yellow-green solution. This solution was cooled to −78° C. and diluted with 100 ml of anhydrous THF which resulted in a white precipitate. Then, a cold (−78° C.) solution of triisopropylborate (145 ml, 0.62 mol) in MTBE (200 ml), under nitrogen was added dropwise over 1.5 h while maintaining the reaction temperature between −78° and −74° C. The resultant reaction mixture was stirred for 1.5 h at −78° C., then allowed to warn to −50° C. over 1 h at which time the cooling bath was removed and the mixture was stirred overnight (16-21 h) which resulted in a white precipitate. The mixture was shaken vigorously with 2M HCl (1000 ml) for 5 minutes and then the resulting layers were separated and the organic layer was dried at reduced pressure to provide a residue. This residue was diluted with MTBE (100 ml), followed by heptane (800 ml) to provide a white powder which isolated by suction filtration and washed 3 times with heptane (300 ml).

Yield: 88 g (98%). $R_f$ 0.45 (95:5 $CH_2Cl_2$/MeOH). $^1$H NMR: δ 0.92 (m, 3H); 1.41 (m, 4H); 1.80 (m, 2H); 4.00 (m, 2H); 6.99 (m, 2H); 7.45-7.63 (m, 3H); 7.67 (m, 2H); 8.24 (d, 1H, J=8.3 Hz). $^{13}$C NMR: 14.01; 22.26; 28.03; 28.77; 39.61; 39.89; 40.17; 40.45; 67.82; 114.77; 125.32; 127.83; 132.93; 134.84; 141.88; 158.71. MS(FD$^+$): m/z 284. IR(CHCl$_3$): 2959, 2952,2874, 1606, 1526, 1500 cm$^{-1}$.

Preparation of Compound 3(a):

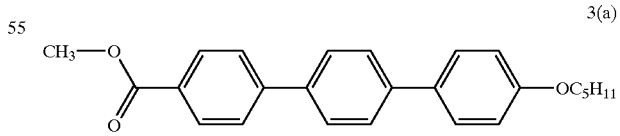

3(a)

A solution of toluene (174 ml) and propanol (20 ml) was degassed 3 times by applying vacuum to the solution for 20-30 seconds followed by purging with $N_2$. A 2M solution of $Na_2CO_3$ was also degassed. The toluene/propanol solution (97 ml) was added to a mixture of methyl 4-iodobenzoate (14.12 g, 53.9 mmol) and Compound 2(a) (15.0 g, 52.8 mmol), followed by a degassed 2M aqueous NACO$_3$ solution (29 ml, 58.0 mmol). The resultant mixture was degassed 2 times for 20-30 seconds each under a positive pressure of N$_2$, followed by the addition of palladium (II) acetate (0.24 g, 1.1 mmol) and triphenylphosphine (0.84 g, 3.2 mmol) and then degassed 2 more times. The reaction mixture was then refluxed under N$_2$ for 5 h resulting in a light-yellow mixture. This mixture was cooled to 23° C. resulting in the formation of a precipitate which was collected by filtration, washed successively with toluene (123 ml), 2:1 MTBE/EtOAc (143 ml), deionized water (123 ml) and 2:1 MTBE/EtOAc (42 ml) and then dried for 16 h in a vacuum oven at 35° C. Yield: 18.7 g (94%). R$_f$ 0.48 (benzene). $^1$H NMR: δ 0.93 (t, 3H, J=6.80 Hz); 1.42 (m, 4H); 1.81 (m, 2H); 3.95 (s, 3H); 4.00 (t, 2H, J=6.48 Hz); 6.97 (d, 2H, J=8.52 Hz); 7.55 (d, 2H, J=8.52 Hz); 7.66 (m, 6H), 8.10 (d, 2H, J=8.20 Hz). MS(FD$^+$): m/z 374. IR(KBr): 2938, 1723 cm$^{-1}$. Analysis for C$_{25}$H$_{26}$O$_3$: Calcd: C, 80.18; H. 7.00; Found: C, 79.91; H. 6.94.

Preparation of Compound 4(a):

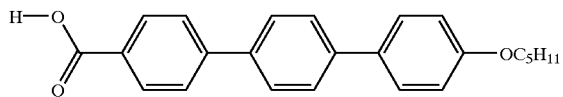

4(a)

A mixture of Compound 3(a) (80 g, 0.21 mol), 5M KOH (160 ml) and cetyltrimethylammonium bromide (4.8 g, 0.013 mol) in xylene (800 ml) was refluxed for 3 h and then cooled to 10° C. and filtered to provide a white solid. This solid was washed 3 times with H$_2$O (500 ml each) to remove the catalyst and most of the base. The resultant material was treated with DME (500 ml). The pH of the solution was adjusted to pH by the addition of 6M HCl (100 ml). The resultant mixture was refluxed for 30 minutes while periodically checking the pH to assure that it remained acidic, then cooled and filtered. The resulting solid was washed successively with MTBE (400 ml) and water (4×400 ml) until the washings were neutral to litmus. Yield: 76 g (98% yield). $^1$H NMR δ 0.89 (t, 3H, J=6.82 Hz), 1.38 (m, 4H), 1.73 (m, 2H), 3.96 (t, 2H, J=6.3 Hz), 6.95 (d, 2H, J=8.56 Hz), 7.57 (d, 2H, J=8.54 Hz), 7.64-7.74 (m, 6H), 8.00 (d, 2H, J=8.21 Hz), 8.09 (s, 1H). MS(FD$^+$) m/z 360. IR(KBr): 2958, 2937, 2872, 1688 cm$^{-1}$. Analysis for C$_{24}$H$_{24}$O$_3$: Calcd: C, 79.97; H. 6.71; Found: C, 80.50; H. 6.77.

Preparation of HOBT Ester of Compound 4(a):

A. Formation of HOBT Mesylate

To a cold (0° C.) mixture of hydroxybenzotriazole hydrate (200 g, 1.48 mol) in anhydrous CH$_2$Cl$_2$ (1.5L), was slowly added anhydrous Et$_3$N (268 ml, 1.92 mol) while maintaining a temperature of 0-10° C., followed by the addition of methanesulfonyl chloride (126 ml, 1.63 mol) while maintaining a temperature of 0-5° C. The resultant mixture was stirred for 3 h at 0° C. and washed successively with cold water (2×1.2L) and brine (1.2L). The combined organic extracts were concentrated at reduced pressure to provide a solid. This solid was recrystallized from CH$_2$Cl$_2$ (100 ml) and heptane (1L). The crystals were collected by suction filtration and washed repeatedly with a total of 1.L of heptane and then dried overnight under high vacuum (0.5 mm Hg). Yield: 245 g (78%) R$_f$ 0.55 (1:1 hexanes/CH$_2$Cl$_2$). $^1$H NMR: δ 3.58 (s, 3H), 746 (t, 1H, J=7.60 Hz), 7.60 (d, 1H, J=8.28 Hz), 7.65 (d, 1H, J=8.56 Hz), 7.68 (d, 1H, J=8.20 Hz), 8.05 (d, 1H, J=8.41 Hz).

B. Formation of HOBT Ester

A mixture of Compound 4(a) (50 g, 0.14 mol) and the material described above in part A (36 g, 0.17 mol) in DMF (650 ml) was treated dropwise with Et$_3$N (25 ml, 0.18 mol), under N$_2$. The resultant mixture was stirred for 4 h at room temperature until all the acid was consumed, as determined by TLC (95:5 CH$_2$Cl$_2$/MeOH). When all the acid was consumed, an aliquot of the reaction mixture (~3 pipes drops) gave a clear homogeneous solution when diluted with 3 ml of 1:1 CH$_2$Cl$_2$/THF. The reaction mixture was then diluted with toluene (500 ml), washed with water (500 ml). The organic layer (containing solid product) was diluted with water (500 ml) and filtered using MTBE for transferring. The solid was rinsed with MTBE (2×400 ml) and dried under vacuum to provide green-white flakes of material. NOTE: This material could be dissolved in THF and filtered to remove any remaining metal contamination. Yield: 61 g (92%). R$_f$ 0.68 (1:1 CH$_2$Cl$_2$/hexanes). $^1$H NMR: δ 0.93 (t, 3H, J=7.0Hz), 1.42 (m, 4H), 1.81 (m, 2H), 4.00 (t, 2H, J=6.53 Hz), 6.99 (d, 2H, J=8.6 Hz), 7.42–7.59 (m, 5H), 7.71 (dd, 4H, J=13.91 Hz, 8.40 Hz), 7.86 (d, 2H, J=8.30 Hz), 8.11 (d, 1H, J=8.31 Hz), 8.35 (d, 2H, J=8.33 Hz). $^{13}$C NMR: δ 14.03, 22.44, 28.18, 28.94, 40.10, 40.37, 68.11, 108.45, 110.11, 114.95, 118.71, 120.48, 123.04, 124.94, 124.99, 127.00, 127.23, 127.51, 127.73, 128.06, 128.82, 128.86, 131.35, 132.30, 137.15, 141.43, 143.54,147.85,159.15, 162.73. MS(FD$^+$): m/z 477. IR(CHCl$_3$): 2960, 2936, 2874, 1783, 1606 cm$^{-1}$. Analysis for C$_{30}$H$_{27}$N$_3$O$_3$: Calcd: C, 75.45; H, 5.70; N, 8.80; Found: C, 75.69; H, 5.58; N, 8.92.

Preparation of Anti-Fungal Compound 1(a):

Deionized water was used throughout the procedure. A mixture of Compound 5(a) (1 g, 23 mmol) and the nucleus of Compound 1(a) (where R is hydrogen—92% pure by HPLC, 19.25 g, 22.2 mmol) in anhydrous DMF (275 ml) was stirred, under N$_2$ for 4 h (until HPLC showed complete consumption of the cyclic peptide starting material). The mixture was filtered through a bed of celite and the filtrate was concentrated under reduced pressure at 35° C. to provide a paste that could be stirred. This paste was poured into MTBE (500 ml) which resulted in the precipitation of a fine powder which was collected by vacuum filtration and dried to provide 27 g of crude material. This material was crushed to a powder with a mortar and pestle, slurried for 5 minutes in toluene (200 ml), suction filtered (slow filtered), rinsed with MTBE (100 ml) and then dried in vacuo to provide a yellow solid. Yield: 23 g (95% pure by HPLC, retention time=7.79 min).

Alternatively, the conversion may be carried out using an excess of the cyclic nucleus (1.1 equiv.). When the reaction is substantially complete, as indicated by HPLC, the crude material (10 g of a powder) is added portion-wise to a vigorously stirred mixture of 9:1 acetone/water (60 ml). Celite (2.5 g, pre-washed with a 9:1 acetone/water mixture) is added to the resultant suspension. After stirring for 2 minutes, the mixture is filtered through a bed of celite (prewashed with 9:1 acetone/water) and the cake is rinsed twice with 9:1 acetone/water (10 ml). The filtrate is poured into a beaker of deionized water (200 ml) while gently swirling the mixture which resulted in the formation of a precipitate. This precipitate is collected by suction filtration, rinsed with H$_2$O (4×25 ml), and then dried in vacuo at room temperature. Yield: 6.81 g (97% pure by HPLC).

The product was further purified using preparatory HPLC chromatography. R$_f$ 0.29 (80:20 CHCl$_3$/MeOH). MS(FAB$^+$): m/z for C$_{58}$H$_{74}$N$_7$O$_7$, Calcd: 1140.5141; Found: 1140.5103. IR(KBr): 3365, 2934, 1632, 1518cm$^{-1}$.

Preparation of a Fructose Complex with Compound 1(a):

A jacketed reactor was charged with 1 equivalent of Compound 1(a), 8 equivalents of fructose and a sufficient quantity of methanol to make 58 mg/ml of Compound 1(a).

The mixture was heated to 50-55° C. until the dissolution was complete. The solution was cooled to 45° C. After seeding at 45° C., the seeded solution was cooled to 25° C. at a cooling rate of −2 degrees/hour. The mixture was further cooled to 0C over 2 hours (cooling rate=−12.5 degrees/hour) and then stirred at 0° C. for 12 hours. The product was isolated by vacuum filtration, washed with cold methanol containing 1% fructose on a weight/weight basis, and then dried 24 hours in a 30° C. vacuum oven. Assays were performed on a gradient HPLC system equipped with a 15 cm×4.6 mm, 3.5 micron particle size Zorbax™ SB-C 18 or XDB-C18 analytical column.

Pharmaceutical Formulations

The following Examples illustrate formulations prepared by the processes of the invention. The Examples are not intended to limit the scope of the invention in any respect and should not be so construed.

The quantity of Compound 1(a) was determined by calculating the theoretical potency needed for the experiments and dividing that value by the "as-is" HPLC potency of the compound.

Example 1

Example 1 illustrates in situ formation of an echinocandin/carbohydrate complex using a fluid bed spray process.

Solution A was prepared by adding 523.70 g of fructose to 760.0 ml of warm purified water while stirring. The solution was then cooled to room temperature.

Solution B was prepared by adding 2,850.0 ml of acetone with stirring to 950.0 ml of purified water cooled to 20–25° C. With stirring, 523.70 g of Compound 1(a) was slowly added to the acetone/water solution.

Solution A was added slowly to solution B with stirring. The clear solution was then sprayed onto a fluidized bed of granular mannitol 2080 (available from SPI Polyols, New Castle, Del.) that had been added to the dryer bowl of a Glatt GPCG-3 fluid bed granulation unit (available from Glatt Air Techniques, Inc.; Ramsey, N.J.). The initial inlet temperature of the unit was set at 30° C. and then increased to 45° C. after the spraying was complete to remove the excess solvent. After drying, the bags were shaken and the contents transferred to a plastic lined container.

The process provided 3,332.7 g (90.9% yield) of a free flowing granular material having a fine texture. Karl Fischer analysis=<1% moisture Bulk density: 0.67 g/ml Tap density after 300 taps of the material=0.79 g/ml. Relative stability of the sprayed granules was determined as the relative ratio of the main degradation products of the control (i.e., bulk Compound 1(a)) versus the test material (i.e., sprayed granules). The degradation products are determined by high performance liquid chromatography (HPLC) and recorded as percent total related substances (% TRS). After storing the sprayed granules in a closed high density polyethylene brown opaque bottle for 1 week at 40° C., the sprayed granules exhibited a lower % TRS (6.50% TRS) than the bulk Compound 1(a) (7.80% TRS) thus indicating an enhancement in thermal stability for the sprayed granules.

After two weeks of storage at 40° C., the sprayed granules continued to exhibit a lower % TRS than the bulk Compound 1(a) (7.42% TRS for the sprayed granules versus 8.79% TRS for Compound 1(a)).

We claim:

1. A process for preparing an oral pharmaceutical formulation comprising the steps of:

(i) mixing an echinocandin compound or echinocandin/carbohydrate complex and at least one carbohydrate in a solvent or mixture of solvents to form a pharmaceutical solution;

(ii) spraying said solution onto a layer of fluidized granular diluent or carrier; and (iii) removing the excess of said solvent or solvents to form granules.

2. The process of claim 1 wherein said echinocandin compound or echinocandin of said echinocandin/carbohydrate complex is represented by the

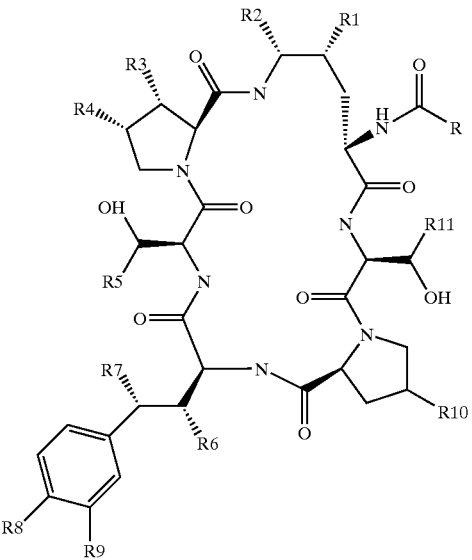

following structure:
wherein:

R is an alkyl group, an alkenyl group, an alkynyl group, an aryl group, heteroaryl group, or combinations thereof;

$R_1$, $R_2$, $R_3$, $R_6$, $R_7$, and $R_{10}$ are independently hydroxy or hydrogen;

$R_4$ is hydrogen, methyl or —$CH_2C(O)NH_2$;

$R_5$ and $R_{11}$ are independently methyl or hydrogen;

$R_4$ is —OH, —$OPO_3H_3$, —$OPO_2HCH_3$, —$OPO_2HCH_3$, or —$OSO_3H$;

$R_9$ is —H, —OH, or -$OSO_3H$; and pharmaceutically acceptable salts thereof.

3. The process of claim 2 wherein $R_4$, $R_5$ and $R_{11}$ are each methyl;

$R_2$ and $R_7$ are independently hydrogen or hydroxy; $R_1$, $R_3$, $R_{15}$ and $R_{10}$ are each hydroxy;

$R_8$ is —OH, —$OPO_3HCH_3$, or —$OPO_2HCH3$;

R is linoleoyl, palmitoyl, stearoyl, myristoyl, 12-methylmyristoyl, 10,12-dimethylmyristoyl, or a group having the general structure:

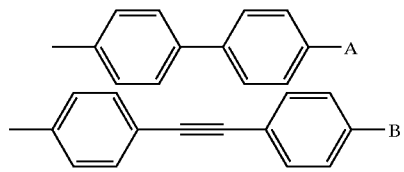

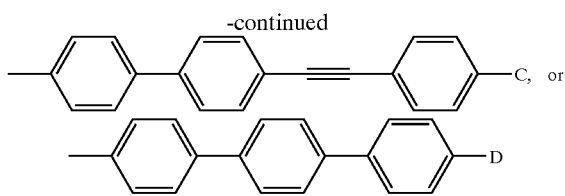

where A, B, C and D are independently hydrogen, $C_1$-$C_{12}$ alkyl, $C_2$-$C_{12}$, alkynyl, $C_1$-$C_{12}$, alkoxy, $C_1$-$C_{12}$ alkylthio, halo, or -O-(CH$_2$)m [O-(CH$_2$)$_n$]$_p$ O-(C$_1$-C$_{12}$ alkyl), or -O-(CHz)q-X-E; m is 2, 3 or 4;

n is 2,3 or 4; p is 0 or 1; q is 2,3 or 4;

X is pyrrolidino, piperidino or piperazino;

E is hydrogen, $C_1$-$C_{12}$ alkyl, $C_3$-$C_{12}$, cycloalkyl, benzyl or $C_3$-$C_{12}$ cycloalkylmethyl.

4. The process of claim 3 wherein $R_2$ and $R_7$ are each hydroxy;

$R_8$ is hydroxy, and

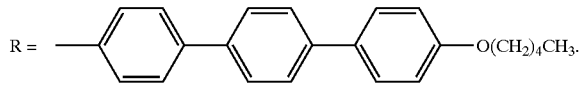

5. The process of claim 1 wherein said at least one carbohydrate is selected from the group consisting of adonitol, arabinose, arabitol, ascorbic acid, chitin, D-cellubiose, 2-deoxy-D-ribose, dulcitol, (S)-(+)-erythrulose, fructose, fucose, galactose, glucose, inositol, lactose, lactulose, lyxose, maltitol, maltose, maltotriose, mannitol, mannose, melezitose, melibiose, microcrystalline cellulose, palatinose, pentaerythritol, raffinose, rhaninose, ribose, sorbitol, sorbose, starch, sucrose, trehalose, xylitol, xylose and hydrates thereof.

6. The process of claim 1 wherein said at least one carbohydrate is selected from the group consisting of L-arabinose, D-arabitol, L-arabitol, 2-deoxy-D-ribose, (S)-(+)-erythrulose, D-fructose, D-(+)-fucose, L-fucose, D-galactose, (β-D-glucose, D-lyxose, L-lyxose, D-maltose, maltotriose, melezitose, palatinose, D-raffinose, D-sorbitol, D-trehalose, xylitol, L-xylose and hydrates thereof.

7. The process of claim 4 wherein said mixture of solvents is acetone and water.

8. The process of claim 7 wherein said acetone is present in an amount from 50% to 70% based on volume relative to said water.

9. The process of claim 1 wherein said granular diluent or carrietis selected from the group consisting of adonitol, arabinose, arabitol, ascorbic acid, chitin, D-cellubiose, 2-deoxy-D-ribose, dulcitol, (S)-(+)-erythrulose, fructose, fucose, galactose, glucose, inositol, lactose, lactulose, lyxose, maltitol, maltose, maltotriose, mannitol, mannose, melezitose, melibiose, microcrystalline cellulose, palatinose, pentaerythritol, raffinose, rhamnose, ribose, sorbitol, sorbose, starch, sucrose, trehalose, xylitol, xylose, polyethylene glycols, hydroxypropyl methylcelluloses, hydroxypropyl methylcellulose phthalates, dextrates and hydrates thereof.

10. The process of claim 1 wherein said granular diluent or carrier is a carbohydrate selected from the group consisting of fructose, glucose, lactose, lactulose; maltitol, maltose, maltotriose, mannitol, mannose, microcrystalline cellulose, hydroxypropyl methylcellulose, hydroxypropyl methylcellulose phthalate, dextrates, dextrin, sorbitol, sorbose, starch, sucrose, trehalose, xylitol, xylose and hydrates thereof.

11. The process of claim 1 wherein said granular diluent or carrier is selected from the group consisting of mannitol, lactose, maltose and hydrates thereof.

12. The process of claim 1 wherein said echinocandin compound is present in said granules in an amount from about 5% to 25% by weight.

13. The process of claim 1 wherein said echinocandin compound is present in said granules in an amount from about 7% to 20% by weight.

14. The process of claim 1 wherein said echinocandin compound is present in said granules in an amount from about 12% to 16% by weight.

15. The process of claim 1 wherein said carbohydrate is present in said granules in an amount from about 5% to 25% by weight.

16. The process of claim 1 wherein said carbohydrate is present in said granules in an amount from about 7% to 20% by weight.

17. The process of claim 1 wherein said carbohydrate is present in said granules in an amount from about 12% to 16% by weight.

18. The process of claim 1 wherein said carrier or diluent is present in said granules in an amount from about 50% to 90% by weight.

19. The process of claim 1 wherein said carrier or diluent is present in said granules in an amount from about 60% to 80% by weight.

20. The process of claim 1 wherein said carrier or diluent is present in said granules in an amount from about 65% to 75% by weight.

21. The process of claim 1 wherein said pharmaceutical solution further comprises excipients selected from the group consisting of surfactants, flavorings, colorants, processing aids, and combinations thereof.

* * * * *